US009212997B2

(12) United States Patent
Gibson et al.

(10) Patent No.: US 9,212,997 B2
(45) Date of Patent: Dec. 15, 2015

(54) SCATTERING SPECTROSCOPY NANOSENSOR

(75) Inventors: Gary Gibson, Palo Alto, CA (US); Zhiyong Li, Foster City, CA (US); Alexandre M. Bratkovski, Mountain View, CA (US); Shih-Yuan Wang, Palo Alto, CA (US); Huei Pei Kuo, Cupertino, CA (US); Steven Barcelo, Palo Alto, CA (US); Zhang-Lin Zhou, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/405,334

(22) PCT Filed: Jul. 29, 2012

(86) PCT No.: PCT/US2012/048753
§ 371 (c)(1),
(2), (4) Date: Dec. 3, 2014

(87) PCT Pub. No.: WO2014/021808
PCT Pub. Date: Feb. 6, 2014

(65) Prior Publication Data
US 2015/0103340 A1 Apr. 16, 2015

(51) Int. Cl.
G01J 3/44 (2006.01)
G01N 21/65 (2006.01)
B82Y 15/00 (2011.01)

(52) U.S. Cl.
CPC ............ *G01N 21/658* (2013.01); *B82Y 15/00* (2013.01); *G01J 3/4412* (2013.01); *G01N 2201/06113* (2013.01); *Y10S 977/902* (2013.01)

(58) Field of Classification Search
CPC .............. G01J 3/02; G01J 3/44; G01N 21/65; G01N 21/658; G01N 2021/656
USPC ............................................... 356/301, 72–73
See application file for complete search history.

(56) References Cited

U.S. PATENT DOCUMENTS

| 6,482,577 B1 | 11/2002 | Sheriff et al. |
| 6,888,629 B1 | 5/2005 | Boss et al. |
| 7,544,461 B2 | 6/2009 | Imai et al. |

(Continued)

FOREIGN PATENT DOCUMENTS

| EP | 1950556 | 7/2008 |
| WO | WO-2011078794 | 6/2011 |

OTHER PUBLICATIONS

Ma, K. et al., In Vivo, Transcutaneous Glucose Sensing Using Surface-enhanced Spatially Offset Raman Spectroscopy: Multiple Rats, Improved Hypoglycemic Accuracy, Low Incident Power, and Continuous Monitoring for Greater Than 17 Days, (Research Paper), Dec. 1, 2011, pp. 9146-9152, vol. 83, No. 23.

*Primary Examiner* — Abdullahi Nur
(74) *Attorney, Agent, or Firm* — Hewlett-Packard Patent Department

(57) ABSTRACT

A scattering spectroscopy nanosensor includes a nanoscale-patterned sensing substrate to produce an optical scattering response signal indicative of a presence of an analyte when interrogated by an optical stimulus. The scattering spectroscopy nanosensor further includes a protective covering to cover and protect the nanoscale-patterned sensing substrate. The protective covering is to be selectably removed by exposure to an optical beam incident on the protective covering. The protective covering is to prevent the analyte from interacting with the nanoscale-patterned sensing substrate prior to being removed.

17 Claims, 6 Drawing Sheets

(56) References Cited

U.S. PATENT DOCUMENTS

| | | |
|---|---|---|
| 7,738,096 B2 | 6/2010 | Zhao et al. |
| 2010/0234684 A1 | 9/2010 | Blume et al. |
| 2011/0165077 A1 | 7/2011 | Qian et al. |
| 2011/0275061 A1 | 11/2011 | Weidemaier et al. |
| 2012/0164745 A1 | 6/2012 | Fu et al. |
| 2012/0242987 A1* | 9/2012 | Liu et al. ............ 356/301 |

* cited by examiner

SCATTERING SPECTROSCOPY NANOSENSOR

CROSS-REFERENCE TO RELATED APPLICATIONS

N/A

STATEMENT REGARDING FEDERALLY SPONSORED RESEARCH OR DEVELOPMENT

N/A

BACKGROUND

Detection and identification (or at least classification) of unknown substances have long been of great interest and have taken on even greater significance in recent years. Among methodologies that hold particular promise for precision detection and identification are various forms of spectroscopy. Spectroscopy may be used to analyze, characterize and identify a substance or material using one or both of an absorption spectrum and an emission spectrum that results when the material is illuminated by a form of electromagnetic radiation (e.g., visible light). The absorption and emission spectra produced by illuminating the material determine a spectral 'fingerprint' of the material. In general, the spectral fingerprint is characteristic of the particular material to facilitate identification of the material. Among the most powerful of optical emission spectroscopy techniques are those based on Raman scattering.

Scattering spectroscopy is an important means of identifying, monitoring and characterizing a variety of analyte species (i.e., analytes) ranging from relatively simple inorganic chemical compounds to complex biological molecules. Among the various types of scattering spectroscopy are methodologies that exploit Raman scattering and scattering due to fluorescence (e.g., fluorescence scattering) from an analyte. In general, scattering spectroscopy employs a signal to excite the analyte that, in turn, produces a response or scattered signal that is dependent on a characteristic (e.g., constituent elements of) the analyte. By detecting and analyzing the scattered signal (e.g., using spectral analysis), the analyte may be identified and even quantified, in some instances.

BRIEF DESCRIPTION OF THE DRAWINGS

Various features of examples in accordance with the principles described herein may be more readily understood with reference to the following detailed description taken in conjunction with the accompanying drawings, where like reference numerals designate like structural elements, and in which.

Figure 1:
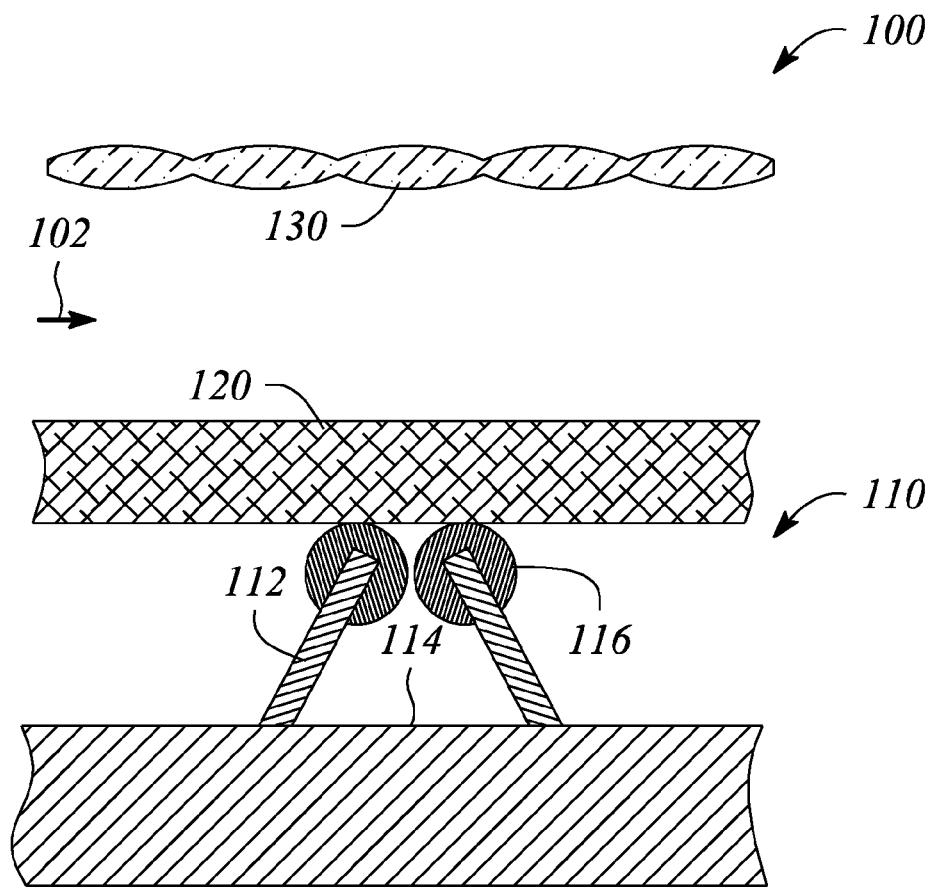
FIG. 1 illustrates a cross sectional view of a portion of a scattering spectroscopy nanosensor, according to an example consistent with the principles described herein.

Certain examples have other features that are one of in addition to and in lieu of the features illustrated in the above-referenced figures. These and other features are detailed below with reference to the above-referenced figures.

DETAILED DESCRIPTION

Examples in accordance with the principles described herein provide detecting or sensing of various analytes using scattering spectroscopy. In particular, examples in accordance with the principles described herein provide sensing of analytes by a scattering spectroscopy nanosensor. In some examples, the scattering spectroscopy nanosensor may provide substantially continuous, in vivo monitoring of analytes (e.g., biological species). Moreover, the scattering spectroscopy nanosensor may provide intimate contact with a fluid (e.g., blood) containing or carrying the analyte without substantial interference with the fluid or with fluid flow.

Examples of the principles described herein employ scattering spectroscopy to detect or sense the presence of the analyte or a target species. Herein, applicable forms of scattering spectroscopy include, but are not limited to, surface enhanced Raman spectroscopy (SERS), surface enhanced coherent anti-stokes Raman scattering (SECARS), various spatially offset and confocal versions of Raman spectroscopy, fluorescence spectroscopy (e.g., using fluorescent labels or tags), and direct monitoring of plasmonic resonances. The scattering spectroscopy may provide detection and in some examples, quantification of the analyte. In particular, the detection or sensing may be provided for an analyte that is either adsorbed onto or closely associated with a sensor surface of the scattering spectroscopy nanosensor, according to various examples. Herein, scattering spectroscopy will generally be described with reference to Raman-scattering optical spectroscopy for simplicity of discussion and not by way of specific limitation, unless otherwise indicated.

Raman-scattering optical spectroscopy or simply Raman spectroscopy, as referred to herein, employs an emission spectrum or spectral components thereof produced by inelastic scattering of photons by an internal structure of a material being illuminated. These spectral components contained in a response signal (e.g., a Raman scattering signal) produced by the inelastic scattering may facilitate determination of the material characteristics of an analyte species including, but not limited to, identification of the analyte. Surface enhanced Raman-scattering (SERS) optical spectroscopy is a form of Raman spectroscopy that employs a Raman-active surface. SERS may significantly enhance a signal level or intensity of the Raman scattering signal produced by a particular analyte species. In particular, in some instances, the Raman-active surface comprises regions associated with the tips of nanostructures such as, but not limited to, nanofingers or nanorods. The tips of the nanorods may serve as nanoantennas to one or both of concentrate an illumination field and amplify a Raman emission leading to further enhancement of the strength of the Raman scattering signal, for example.

In some examples of SERS, a SERS surface comprising a plurality of nanorods is configured to enhance production and emission of the Raman scattering signal from an analyte. Specifically, an electromagnetic field associated with and surrounding the nanorods (e.g., tips of the nanorods) in a 'Raman-active' configuration may enhance Raman scattering from the analyte, in some examples. A relative location of the nanorods themselves as well as tips of the nanorods in the Raman-active configuration may provide enhanced Raman scattering.

A 'nanorod' or equivalently a 'nanofinger' herein is defined as an elongated, nanoscale structure having a length (or height) that exceeds by more than several times a nanoscale cross sectional dimension (e.g., width) taken in a plane perpendicular to the length (e.g., length>about 5 times the width). In general, the length of the nanorod is much greater than the nanorod width or cross sectional dimension. In some examples, the length exceeds the cross sectional dimension (or width) by more than a factor of 5 or 10. For example, the width may be about 40 nanometers (nm) and the height may be about 400 nm. In another example, the width at a base of the nanorod may range between about 20 nm and about 100 nm and the length may be more than about a 1 micrometer (μm). In another example, the nanorod may be conical with a base having a width ranging from between about 100 nm and about 500 nm and a length or height that may range between about one half (0.5) and several micrometers.

In various examples, nanorods of the plurality may be grown (i.e., produced by an additive process) or produced by etching or a subtractive process. For example, the nanorods may be grown as nanowires using a vapor-liquid-solid (VLS) growth process. In other examples, nanowire growth may employ one of a vapor-solid (V-S) growth process and a solution growth process. In yet other examples, growth may be realized through directed or stimulated self-organization techniques such as, but not limited to, focused ion beam (FIB) deposition and laser-induced self assembly. In another example, the nanorods may be produced by using an etching process such as, but not limited to, reactive ion etching, to remove surrounding material leaving behind the nanorods. In yet other examples, various forms of imprint lithography including, but not limited to, nanoimprint lithography as well as various techniques used in the fabrication of micro-electromechanical systems (MEMS) and nano-electromechanical systems (NEMS) are applicable to the fabrication of the nanorods and various other elements described herein.

A 'nanoparticle' herein is defined as a nanoscale structure having substantially similar dimensions of length, width and depth. For example, the shape of a nanoparticle may be a cylinder, a sphere, an ellipsoid, or a faceted sphere or ellipsoid, or a cube, an octahedron, a dodecahedron, or another polygon. The nanoparticle may comprise a substantially irregular three-dimensional shape, in other examples. The size of the nanoparticle may range from about 5 nm to about 200 nm, for example, in diameter or dimension. In some examples, the nanoparticle dimensions may be within a range of about 50 nm to about 100 nm, or about 25 nm to about 100 nm, or about 100 nm to about 200 nm, or about 10 nm to about 150 nm, or about 20 nm to about 200 nm. Further as defined herein, the 'nanoparticle' is distinguished from a 'nanoparticle catalyst' or 'catalyst nanoparticle' and a layer or coating of nanoparticles, according to some examples.

Herein a 'lens' is defined as a purpose-formed optical structure configured to focus or otherwise direct a beam of light or an optical signal. The lens may be a separate, isolated lens, in some examples. Alternatively, the lens may be one of a plurality of lenses in an array. For example, the lens may be a lenslet of an array of lenslets. An 'integral' lens is defined as a lens that is formed or otherwise provided as an integral part of another structure. By 'purpose-formed' is it meant that the optical structure is created for an intended purpose as opposed to merely providing a function that is inherent. For example, the lens may be a purpose-formed optical structure designed and fabricated to provide a specific numerical aperture, focal length, etc.

Further, as used herein, the article 'a' is intended to have its ordinary meaning in the patent arts, namely 'one or more'. For example, 'a nanosensor' means one or more nanosensors and as such, 'the nanosensor' means 'the nanosensor(s)' herein. Also, any reference herein to 'top', 'bottom'. 'upper', 'lower', 'up', 'down', 'front', 'back', 'left' or 'right' is not intended to be a limitation herein. Herein, the term 'about' when applied to a value generally means within the tolerance range of the equipment used to produce the value, or in some examples, means plus or minus 10%, or plus or minus 5%, or plus or minus 1%, unless otherwise expressly specified. Moreover, examples herein are intended to be illustrative only and are presented for discussion purposes and not by way of limitation.

FIG. 1 illustrates a cross sectional view of a portion of a scattering spectroscopy nanosensor 100, according to an example consistent with the principles described herein. The scattering spectroscopy nanosensor 100 is configured to sense an analyte in a fluid flowing through or adjacent to the scattering spectroscopy nanosensor 100. An arrow 102 in FIG. 1 illustrates a fluid flow direction past the scattering spectroscopy nanosensor 100, for example.

As illustrated in FIG. 1, the scattering spectroscopy nanosensor 100 comprises a nanoscale-patterned sensing substrate 110. The nanoscale-patterned sensing substrate 110 is configured to produce an optical scattering response signal indicative of the presence of an analyte, according to various examples. In particular, the optical scattering response signal may be produced when the nanoscale-patterned sensing substrate 110 is interrogated by an optical stimulus (e.g., a optical stimulus beam or signal), according to various examples.

In some examples, the fluid flowing past the nanoscale-patterned sensing substrate 110 is flowing in a fluid conduit. For example, the fluid conduit may comprise a blood vessel and the fluid may comprise blood. The scattering spectroscopy nanosensor 100 may provide in vivo sensing of the analyte carried in the blood, for example. In other examples, the fluid conduit carrying blood may be a tube connected to a blood vessel (e.g., external to an organism), in which case the analyte sensing may not be in vivo.

In some examples, the nanoscale-patterned sensing substrate 110 comprises a surface enhanced Raman spectroscopy (SERS) substrate. In these examples, the optical scattering response signal may comprise a SERS scattering signal. In other examples, the nanoscale-patterned sensing substrate 110 may comprise another optical scattering substrate including, but not limited to, a substrate that uses one or both of infrared spectroscopy and fluorescence spectroscopy. For example, the nanoscale-patterned sensing substrate 110 may comprise tagged structures configured to produce a fluorescence signal when the analyte is present.

In some examples, the SERS sensing substrate may comprise a plurality of nanorods 112 arranged in an array. The nanorods 112 have a free end that is opposite to an end that is attached to a support 114, according to some examples. In some examples, the support 114 may comprise a substrate that provides support for the nanorods 112. In some examples, the nanorods 112 are rigidly attached to the support 114 at the fixed end. In other examples, the nanorods 112 are indirectly attached to the support 114 through an intermediate material or layer, for example.

In some examples, at least some of the nanorods 112 in the array have a metallic tip at the free end. The metallic tip may be configured to either absorb or adsorb the analyte, for example. In some examples, the metallic tip at the free end of the nanorod 112 may be functionalized. In particular, the nanorod may be functionalized to preferentially bind to or provide selective absorption of a particular analyte species, for example.

In some examples, a nanorod 112 of the plurality may comprise a nanoparticle 116 attached to the free end in a vicinity of the tip. In some examples, a material of the nanoparticle 116 may differ from a material of the nanorod 112. For example, the tip may include a metal (e.g., gold) nanoparticle 116 that remains from nanorod growth, for example. In some of these examples, the nanoparticle 116 may be configured to one or both of enhance Raman scattering and facilitate selective analyte adsorption (e.g., by functionalization). In particular, in some examples, the nanoparticle 116 comprises a material suitable for Raman enhancement. For example, the nanoparticle 116 may comprise a material such as, but not limited to, gold, silver, platinum, aluminum and copper.

In some examples, a nanorod 112 of the plurality comprises a plurality of the nanorod 112. The plurality of the nanorod 112 may be arranged in a bundle, for example. As used herein, a 'bundle' is defined as a relatively small grouping or a small array. For example, the bundle may comprise two, three, four, five, six or more nanorods 112. The nanorods 112 of the bundle may be arranged such that the free ends and the fixed ends of the nanorods 122, respectively, are located at vertices of a polygon or a polyhedron (e.g., a digon, a trigon, a tetragon, a pentagon, a hexagon, and so on), according to various examples. In another example, a bundle may have up to about ten nanorods 112. In yet another example, the bundle may have less than about fifteen nanorods 112. Moreover, there may be a plurality of such bundles, in some examples.

Figure 2:
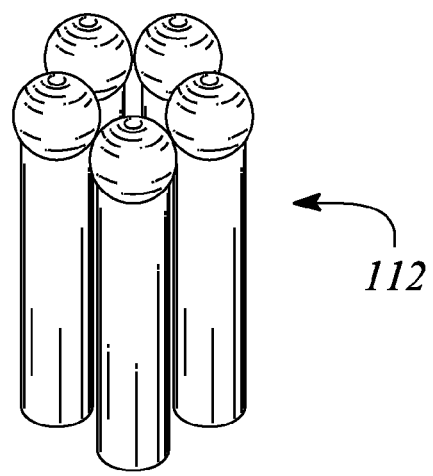
FIG. 2 illustrates a perspective view of a bundle of a plurality of nanorods, according to an example consistent with the principles described herein.

FIG. 2 illustrates a perspective view of a bundle of a plurality of nanorods 112, according to an example consistent with the principles described herein. The bundle illustrated in FIG. 2 comprises five nanorods 112. Further as illustrated, the plurality of nanorods 112 of the bundle is arranged as a pentagon. In other examples, the plurality of nanorods 112 may be arranged in a larger array (not illustrated). A larger array may have several tens of nanorods, hundreds of nanorods or even more, for example. The array, including both small arrays (e.g., bundles) and large arrays, may include, but is not limited to, a linear array or one-dimensional (1-D) array or a two-dimensional (2-D) array (e.g., a rectilinear array, a circular array, etc.).

The nanorods 112 in either the bundle or the array may be either touching one another or spaced apart from one another.

For example, tips of the nanorods 112 in the bundle may be substantially touching or in close proximity, separated by a gap of a about a few nanometers or less. Further, nanorods 112 in either the bundle or the array may be tilted toward one another (e.g., see FIG. 1). The tilting may facilitate contact between the tips of the nanorods 112, for example. A spacing between nanorods 112 of the plurality when spaced apart within the bundle or the array may be either regular (i.e., a periodic spacing) or irregular (e.g., a substantially random spacing). For example, the nanorods 112 of the plurality may be arranged in a pair of substantially parallel, regular-spaced, linear arrays.

In some examples, the nanorod 112 may comprise a semiconductor. For example, the semiconductor may comprise doped or undoped (i.e., substantially intrinsic) silicon (Si), germanium (Ge) or an alloy of Si and Ge. In other examples, the semiconductor may comprise one or more of gallium arsenide (GaAs), indium gallium arsenide (InGaAs), gallium nitride (GaN), or various other III-V, II-VI, and IV-VI compound semiconductors. In other examples, the nanorod 112 may comprise a plastic or a polymer such as, but not limited to, polyurethane, poly(tert-butyl methacrylate) (P(tBMA)), polymethylmethacrylate (PMMA), polystyrene, polycarbonate or related plastics. In yet other examples, the nanorod 112 may comprise a metal such as, but not limited to, gold, silver, platinum, other noble metals, aluminum copper, or an alloy or a combination of two or more metals.

Referring again to FIG. 1, the scattering spectroscopy nanosensor 100 further comprises a protective covering 120. The protective covering 120 is configured to cover and protect the nanoscale-patterned sensing substrate 110 according to various examples. For example, the protective covering 120 may prevent a fluid as well as any materials (e.g., an analyte) carried by the fluid from reaching and substantially affecting the nanoscale-patterned sensing substrate 110 while the protective covering 120 is in place. The protective covering 120 may substantially prevent the fluid or materials carried by the fluid from damaging the nanoscale-patterned sensing substrate 110, for example. Further, the protective covering 120 may render the nanoscale-patterned sensing substrate 110 substantially inactive and incapable of producing the optical scattering response signal while the protective covering 120 is in place, according to various examples. For example, the protective covering 120 may prevent the analyte from interacting with the nanoscale-patterned sensing substrate 110 to produce the optical scattering response signal when interrogated by the optical stimulus.

According to some examples, the protective covering 120 is a membrane adjacent to a surface. For example, the protective covering 120 may be a membrane that is positioned on a first or top surface of the nanoscale-patterned sensing substrate 110, as illustrated in FIG. 1. The membrane may be position on top of nanoparticle 116 of the nanorod 112, for example. In other examples (not illustrated), the protective covering 120 may be a layer that substantially bonds to and fills in around features of the nanoscale-patterned sensing substrate 110. For example, the protective covering 120 may be applied as a liquid to cover and substantially fill spaces between the features (e.g., nanorods) of the nanoscale-patterned sensing substrate 110. The liquid may be cured into a solid to form the protective covering 120 that substantially encapsulates the features of the nanoscale-patterned sensing substrate 110 (not illustrated in FIG. 1), for example.

Further, according to various examples, the protective covering 120 is configured to be selectably removable. In particular, the protective covering 120 is selectively removable by exposure to an optical beam incident on the protective covering 120, according to various examples. In some examples, exposure to the optical beam selectably removes only a portion of the protective covering 120 in a vicinity of the optical beam. For example, the portion removed may be a portion that is within a half-power (e.g., 3 dB) beam width of the optical beam. In another example, the protective covering portion that is selectably removed is a portion of the protective covering 120 that receives a predetermined optical energy or intensity over a predetermined time period from the optical beam exposure. In other examples, the entire protective covering 120 is selectably removed by the optical beam exposure.

For example, exposure to the optical beam may facilitate removal of a portion of the protective covering 120 by ablation of the protective covering 120. The optical beam may substantially 'burn' away the exposed portion of the protective covering 120, for example. The optical beam may be a laser beam of sufficient power within the optical beam width to ablate the protective covering 120, according to some examples.

In another example, the protective covering 120 may be selectably removable by one or both of a photo-induced alteration and a thermal-induced alteration of an exposed portion of the protective covering 120. For example, exposure to the optical beam may render the protective covering 120 substantially more soluble in a fluid than prior to exposure. The exposed portion of the protective covering 120 may be dissolved and removed by the fluid (e.g., flowing past the exposed portion) after exposure to the optical beam, according to some examples. In some examples, the photo-induced alteration or the thermal-induced alteration may comprise a depolymerization. For example, the protective covering 120 may be substantially similar to a positive photoresist that becomes soluble when exposed to the optical beam. In other examples, the photo-induced or thermal-induced alteration may comprise a state transition (e.g., solid to liquid) of a material of the protective covering 120 as opposed to or in addition to depolymerization. For example, the material of the protective covering 120 may be melted by exposure to the optical beam (e.g., a thermal-induced state transition). In yet other examples, the photo-induced or thermal-induced alteration may take place by another mechanism.

In another example, the protective covering 120 may be selectably removable by one or both of a photo-induced change and a thermal induced change in adhesion between the protective covering 120 and the nanoscale-patterned sensing substrate 110. For example, the optical beam may serve to break down or otherwise alter the adhesion characteristics of a layer of adhesive (not illustrated) between the protective covering 120 and the nanoscale-patterned sensing substrate 110. The altered adhesion may facilitate one or both of local and global release of the protective covering 120, according to various examples.

In yet other examples, another mechanism of optical beam-induced selective removal of the protective covering 120 may be employed including, but not limited to, one or both of a photo-induced chemical reaction and a thermal-induced chemical reaction. For example, the optical beam may facilitate chemical reactions between components of the protective covering 120. The chemical reactions may lead to a breakdown (e.g., a local disassembly) of the protective layer 120. In another example, the protective layer 120 may comprise a plurality of layers. Exposure to the optical beam may lead to chemical reactions between the layers that lead to selective removal of the protective layer 120, for example.

Selective removable of the protective covering 120 exposes a portion of the underlying nanoscale-patterned sensing substrate 110. The exposed portion is rendered accessible to the fluid and any analyte that may be present therein. In particular, the exposed portion of the nanoscale-patterned sensing substrate 110 is rendered 'active' and thus capable of producing the optical scattering response signal when interrogated by the optical stimulus, according to various examples.

According to various examples, the optical beam may comprise substantially any frequency or combination of frequencies that may produce the selective removal of the protective layer 120. In particular, the optical beam may comprise frequencies in the infrared (IR) spectrum, in some examples. The IR spectrum may facilitate penetration of tissue or other intervening material by the optical beam, in some examples. Penetration characteristics of the optical beam may be important when the scattering spectroscopy nanosensor 100 is employed as an implantable nanosensor (e.g., in a blood vessel) for in vivo sensing of an analyte, for example. In other examples, such other frequencies including, but not limited to, frequencies in the visible and ultraviolet (UV) spectrum may be employed in the optical beam.

In some examples, a frequency of the optical beam may be substantially similar to a frequency of the optical stimulus used to interrogate the nanoscale-patterned sensing substrate 110. For example, a difference between the optical beam used to provide selective removal of the protective covering 120 and the optical stimulus use to interrogate the nanoscale-patterned sensing substrate 110 may be a power level of the optical beam or signal. The difference may merely be a difference in time, in other examples. In particular, during a first period of time, a particular optical signal may serve as the optical beam to selectively remove the protective covering 120. Then, in a second (e.g., subsequent) period of time, the particular optical signal may serve as the optical stimulus, according to some examples.

Referring again to FIG. 1, in some examples, the scattering spectroscopy nanosensor 100 further comprises a lens 130. In particular, the lens 130 is integral with the scattering spectroscopy nanosensor 100, according to various examples. As illustrated, the integral lens 130 is a lenslet of a plurality of lenslets in a lenslet array. In some examples, the integral lens 130 is configured to focus the optical beam onto the protective covering 120. In some examples, the integral lens 130 is configured to focus the optical stimulus on a portion of the nanoscale-patterned sensing substrate 110 exposed by selective removal of the protective cover 120. In some examples, the integral lens 130 is configured to collect the optical scattering response signal produced by interrogation of the nanoscale-patterned sensor substrate 110 using the optical stimulus. In some examples, the integral lens 130 provides two or more of focusing the optical beam, focusing the optical stimulus and collecting the optical scattering response signal. For example, the integral lens 130 may provide a depth of focus that is larger than a separation between the protective covering 120 and the nanoscale-patterned sensing substrate 110 (e.g., a surface of each).

For example, the integral lens 130 may focus the optical beam to provide a predetermined optical intensity at the protective covering 120 to facilitate selective removal thereof. The optical beam may be at a lower intensity prior to the integral lens 130 to avoid damaging material such as, but not limited to, tissue through which the optical beam passes to reach the lens 130, for example. In another example, the integral lens 130 may collect the optical scattered response signal to facilitate detection thereof by a detector, for example. In some examples, the lens 130 may substantially collimate the collected optical scattered response signal to facilitate the detection. In other examples, the lens 130 may focus the collected optical scattered response signal to facilitate the detection.

In another example, the optical beam and the optical stimulus may be substantially coaxial. For example, a common illumination source (e.g., a laser) may be used to produce both of the optical beam and the optical stimulus. The integral lens 130 may focus the optical beam on a particular portion of the protective covering 120 to selectively remove the particular portion. The integral lens 130 may then focus the optical stimulus onto the nanoscale-patterned sensor substrate 110. Since the coaxial optical beam and the optical stimulus are focused by the same integral lens 130, the optical stimulus being focused by the integral lens 130 substantially interrogates the exposed portion of the nanoscale-patterned sensor substrate 110 that resulted from the selective removal of the protective covering 120. Hence, the integral lens 130 substantially provides a self-alignment of the optical stimulus with respect to the optical beam.

Figure 3A:
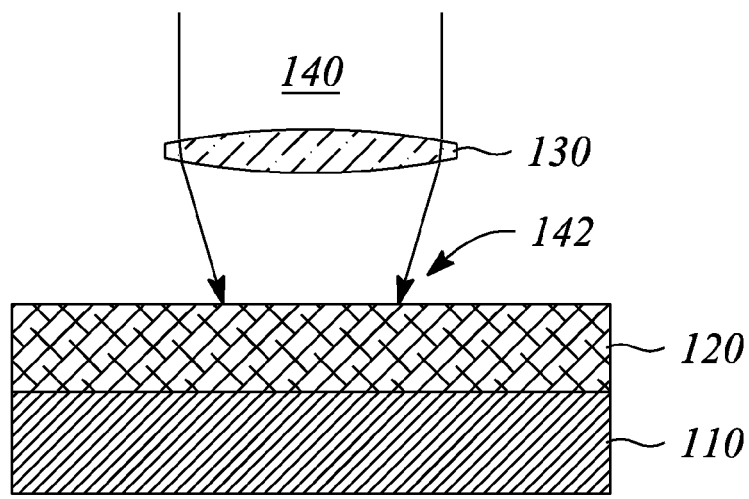
FIG. 3A illustrates a cross sectional view of the scattering spectroscopy nanosensor, according to an example consistent with the principles described herein.

FIG. 3A illustrates a cross sectional view of the scattering spectroscopy nanosensor 100, according to an example consistent with the principles described herein. In particular, illustrated in FIG. 3A are the nanoscale-patterned sensing substrate 110 and the protective covering 120 on top of the nanoscale-patterned sensing substrate 110. Further illustrated is the integral lens 130 above and spaced apart from the nanoscale-patterned sensing substrate 110 and the protective covering 120. As illustrated, an optical beam 140 is depicted passing through the integral lens 130. Further, the optical beam is focused onto the protective covering 120 by the integral lens 130, as illustrated. Focusing may reduce a diameter of the optical beam 140 to produce a relatively small spot 142 of focused optical energy on the protective covering 120, for example. The small spot 142 may expose less than about 1 square micron (1 $\mu m^2$) of the protective covering 120, according to some examples.

Figure 3B:
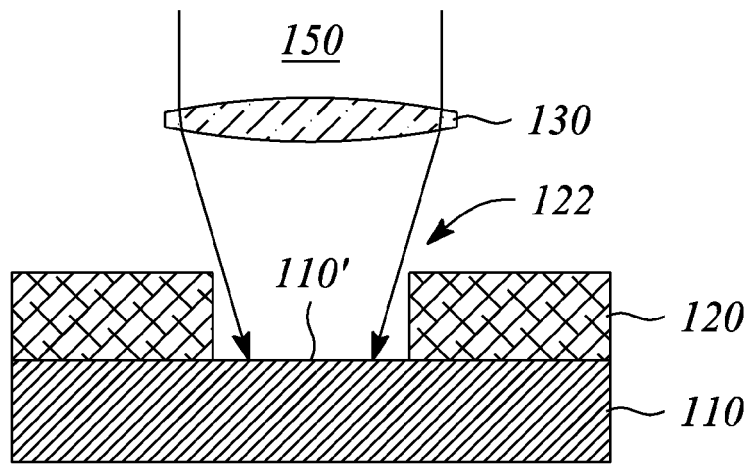
FIG. 3B illustrates a cross sectional view of the scattering spectroscopy nanosensor illustrated in FIG. 3A, according to an example consistent with the principles described herein.

FIG. 3B illustrates a cross sectional view of the scattering spectroscopy nanosensor 100 illustrated in FIG. 3A, according to an example consistent with the principles described herein. In particular, FIG. 3B illustrates the scattering spectroscopy nanosensor 100 following exposure to the optical beam 140. As illustrated, a portion of the protective covering 120 has been selectably removed by the optical beam 140. For example, the selectively removed portion of the protective covering 120 is illustrated as a hole 122 through the protective covering 120 in FIG. 3B. The hole 122 exposes a portion 110' of the underlying nanoscale-patterned sensor substrate 110. Further, FIG. 3B illustrates an optical stimulus 150 incident on the portion 110' of the nanoscale-patterned sensor substrate 110 exposed by the selective removal of the protective covering 120. As illustrated, the optical stimulus 150 passes through and is focused by the integral lens 130. Further, the integral lens 130 focuses the optical stimulus 150 onto substantially the same location as that of the focused spot 142 of the optical beam 140. As such, the optical stimulus 150 is substantially 'self-aligned' with the optical beam 140 by the integral lens 130, as illustrated.

Figure 3C:
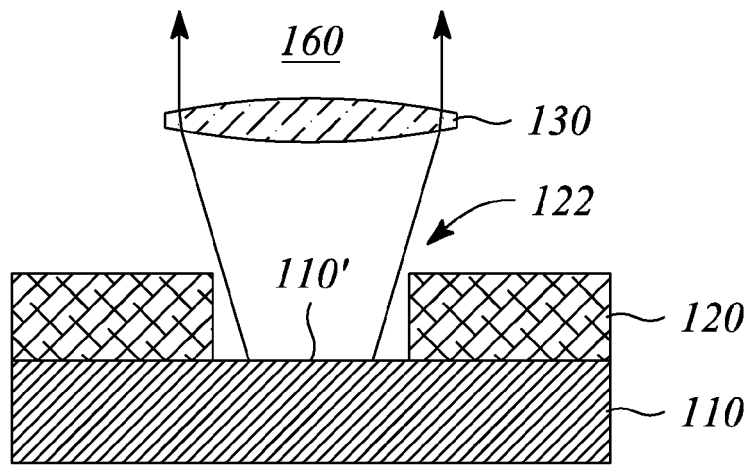
FIG. 3C illustrates a cross sectional view of the scattering spectroscopy nanosensor illustrated in FIG. 3B, according to an example consistent with the principles described herein.

FIG. 3C illustrates a cross sectional view of the scattering spectroscopy nanosensor 100 illustrated in FIG. 3B, according to an example consistent with the principles described herein. In particular, FIG. 3C illustrates the optical scattering response signal 160 radiating from the exposed portion 110' of the nanoscale-patterned sensor substrate 110 (e.g., through the hole 122 in the protective covering 120) after stimulus with the stimulus signal 150. The optical scattering response signal 160 is illustrated as being intercepted or collected and substantially collimated by the integral lens 130. In other examples (not illustrated), the integral lens 130 may focus the collected optical scattering response signal 160 at some focal length (e.g., to coincide with an aperture of a detector) instead of collimating the collected optical scattering response signal 160. Note, while the optical scattering response signal is generally only produced during illumination of the nanoscale-patterned sensing substrate 110 by the optical stimulus 150, the optical stimulus is omitted from FIG. 3C for simplicity of illustration.

In some examples, a direction of one or both of the optical beam 140 and the optical stimulus 150 may be varied (e.g., in a time sequence) to activate different areas or regions of the nanoscale-patterned sensor substrate 110. For example, the optical beam 140 and optical stimulus 150 may be initially directed to a first region of the nanoscale-patterned sensor substrate 110. Once exposed by the optical beam 140, analyte at the first region may produce the optical scattering response signal 160 when illuminated by the optical stimulus 150, for example. At some later time, the direction of the optical beam 140 and optical stimulus 150 may be changed to be expose and illuminate a second region of the nanoscale-patterned sensor substrate 110. Successive changes in the direction of the optical beam 140 and optical stimulus 150 over time may facilitate using the nanoscale-patterned sensor substrate 110 in a time-multiplexed manner to perform analyte sensing as a sequence of substantially separate sensing events over a substantially long period of time, according to some examples.

In some examples, the scattering spectroscopy nanosensor 100 further comprises a stent. The nanoscale-patterned sensing substrate 110 may be disposed on a surface of the stent, according to various examples. The stent is configured to be implanted inside a fluid conduit (not illustrated), according to some examples. In some examples, the stent comprises a hollow structure that is configured to allow the fluid flowing in the fluid conduit to pass through an interior portion (e.g., a hollow interior) of the stent. For example, the fluid may flow into a first end and along a path through the hollow interior that is substantially aligned with a central axis of the stent and then exit at a second end of the stent. In other examples, the stent may not be hollow in which case the stent is configured to allow for fluid flow around but not through the stent. In yet other examples, the stent may comprise a hollow or a substantially hollow structure that is configured to provide for fluid flow both through the hollow interior and around an outside of the stent.

In some examples, the stent may comprise a tubular structure that is substantially hollow. A cross sectional shape of the tubular structure may be either substantially circular (e.g., circular, elliptical, semi-circular, etc.) or substantially non-circular (e.g., rectangular, square, generally polygonal or faceted, etc.), according to various examples. In some examples, the tubular structure may have a fixed or substantially fixed diameter. In other examples, the tubular structure may be configured to expand and substantially conform to an inside surface or wall of the fluid conduit. For example, the fluid conduit may comprise a blood vessel and the tubular structure of the stent may be expandable to conform to an inside surface of the blood vessel.

In some examples, expansion of the tubular structure of the stent may facilitate retaining or securing the stent in place within the fluid conduit. For example, the expansion may press portions of the tubular structure of the stent against a wall of the fluid conduit such that friction between the stent and the fluid conduit wall resists a force imparted on the stent by the fluid flowing within the fluid conduit. Further, the expansion of the tubular structure of the stent may facilitate fluid flow through an interior of the tubular structure. For example, the expanded substantially tubular structure may provide an opening through the tubular structure that is similar in diameter to that of the fluid conduit itself. As such, the stent may not interfere in a substantial manner with fluid flow in the fluid conduit, according to some examples.

Figure 4:
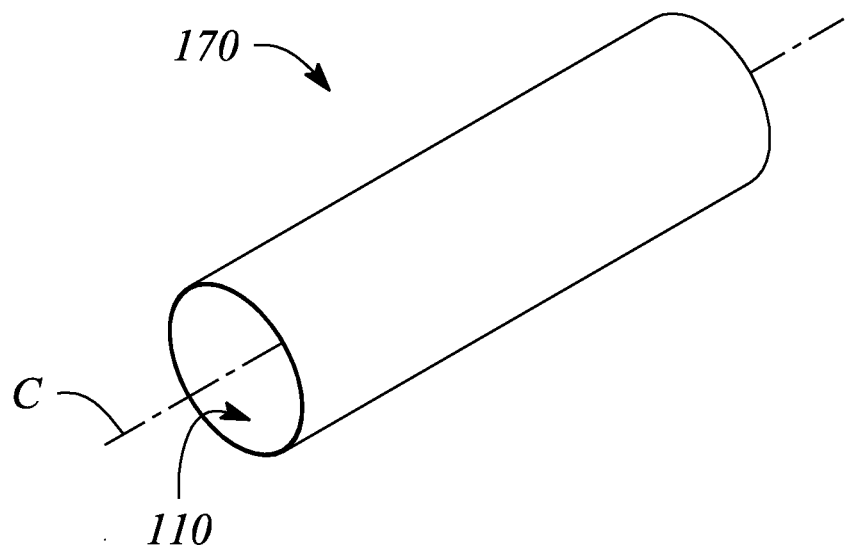
FIG. 4 illustrates a perspective view of a stent of a scattering spectroscopy nanosensor, according to an example consistent with the principles described herein.

FIG. 4 illustrates a perspective view of a stent 170 of the scattering spectroscopy nanosensor 100, according to an example consistent with the principles described herein. As illustrated in FIG. 4, the stent 170 comprises a substantially tubular structure. The substantially tubular structure may comprise tube of either a rigid or a semi-rigid material, in some examples. For example, the tube may comprise a metal tube (e.g., stainless steel, nitinol alloy, etc.) or a polymer tube. The tube may have an outside diameter that is smaller, and in some examples much smaller, than an inside diameter of the fluid conduit, according to some examples. The nanoscale-patterned sensing substrate 110 may be located on an inside surface (e.g., facing a central axis C) of the stent 170, for example.

Figure 5A:
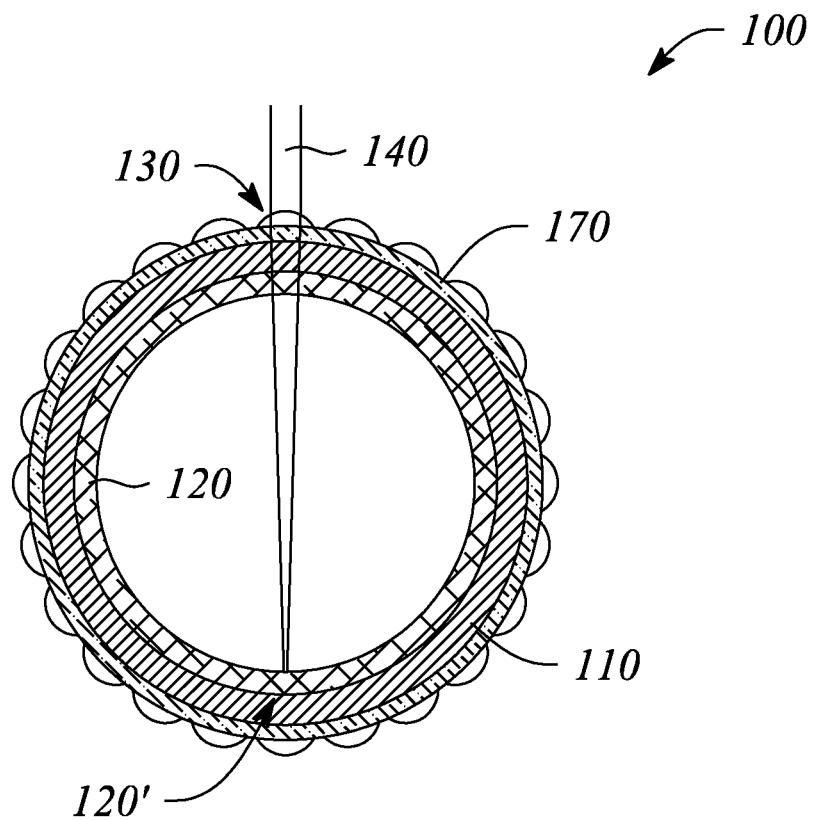
FIG. 5A illustrates a cross sectional view of a scattering spectroscopy nanosensor, according to an example consistent with the principles described herein.
Figure 5B:
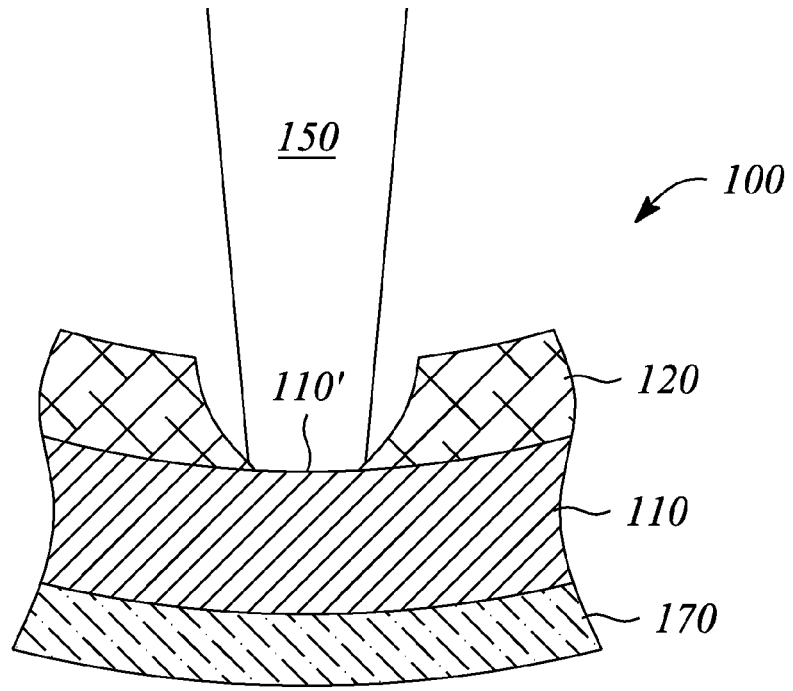
FIG. 5B illustrates a cross sectional view of a magnified portion of the scattering spectroscopy nanosensor of FIG. 5A, according to an example consistent with the principles described herein.

FIG. 5A illustrates a cross sectional view of a scattering spectroscopy nanosensor 100, according to an example consistent with the principles described herein. FIG. 5B illustrates a cross sectional view of a magnified portion of the scattering spectroscopy nanosensor 100 of FIG. 5A, according to an example consistent with the principles described herein. In particular, the cross sectional views illustrated in FIGS. 5A and 5B depict a cross section through the scattering spectroscopy nanosensor 100 that is substantially perpendicular to a central axis of the scattering spectroscopy nanosensor 100 (e.g., perpendicular to central axis C of the stent 170 of FIG. 4).

As illustrated in FIG. 5A, the nanoscale-patterned sensor substrate 110 and the protective covering 120 are disposed on an inside surface of a stent 170 of the scattering spectroscopy nanosensor 100. FIG. 5A further illustrates an integral lens 130 on an outside surface of the stent 170. For example, the stent 170 may comprise a material that is substantially optically transparent. The integral lens 130 may be formed from a material of the stent 170, according to some examples. In other examples, the integral lens 130 may be separately provided and applied (e.g., glued or welded) to the outside surface of the stent 170.

According to some examples of the scattering spectroscopy nanosensor 100 illustrated in FIG. 5A, the protective covering 120 may be selectively removed by an optical beam 140 that passes through the lens 130 to be focused on a portion 120' of the protective covering 120 on the inside surface of the stent 170 opposite the integral lens 130. Similarly, an optical stimulus 150 may be also be focused by the integral lens 130 onto a portion 110' of the nanoscale-patterned sensing substrate 110 that is exposed by the selective removal of the protective covering 120, as illustrated in FIG. 5B. Specifically, FIG. 5B illustrates the protective covering 120 having been removed to expose the nanoscale-patterned sensing substrate portion 110'.

In some examples, one or both of the optical beam 140 and optical stimulus 150 may pass through a portion of the stent wall, the nanoscale-patterned sensing substrate 110 and the protective covering 120 immediately adjacent to the lens 130 (e.g., as illustrated in FIG. 5A) without substantial interference and without affecting the immediately adjacent protective covering 120. For example, the stent wall, the nanoscale-patterned sensing substrate 110 and protective covering 120 may be substantially transparent to one or both of the optical beam 140 and the optical stimulus 150, at least when the optical beam 140 and the optical stimulus 150 are substantially unfocussed. Further, an intended affect of one or both of the optical beam 140 and the optical stimulus 150 may manifest only as a result of focusing by the lens 130 (e.g., as at the portion 120'), according to some examples. For example, removal of the protective covering 120 may only occur at or above a particular power density of the optical beam 140. The energy density for removal may be provided by focusing at the portion 120' but not where the optical beam 140 passes through the lens-adjacent region of the protective covering 120, for example. In other examples (not illustrated), the lens 130 may focus one or both of the optical beam 140 and optical stimulus 150 on the stent wall immediately adjacent to the lens 130.

Figure 6:
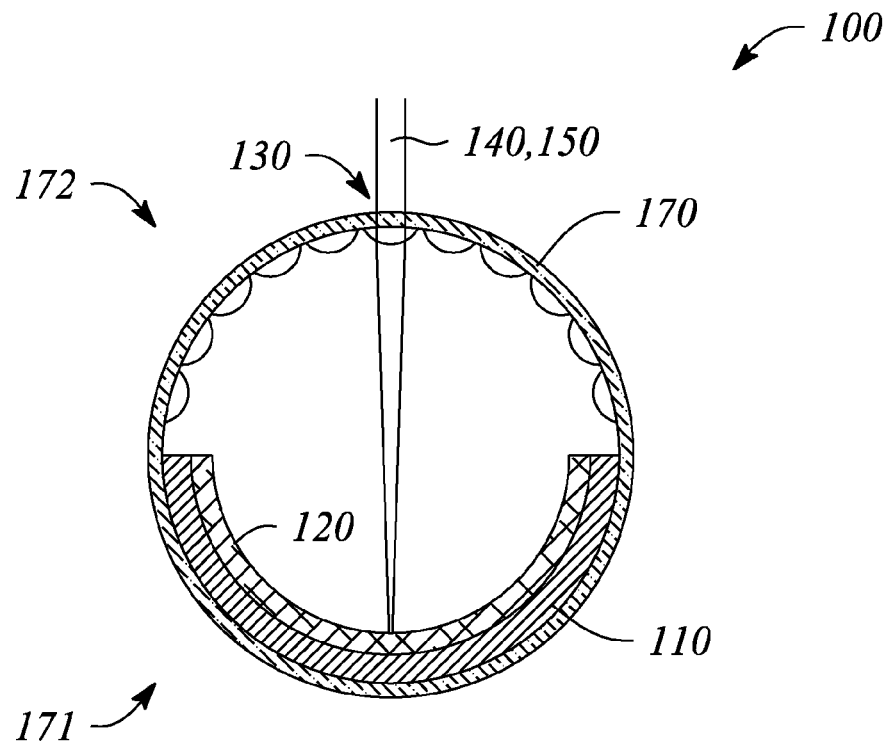
FIG. 6 illustrates a cross sectional view of a scattering spectroscopy nanosensor, according to another example consistent with the principles described herein.
Figure 7:
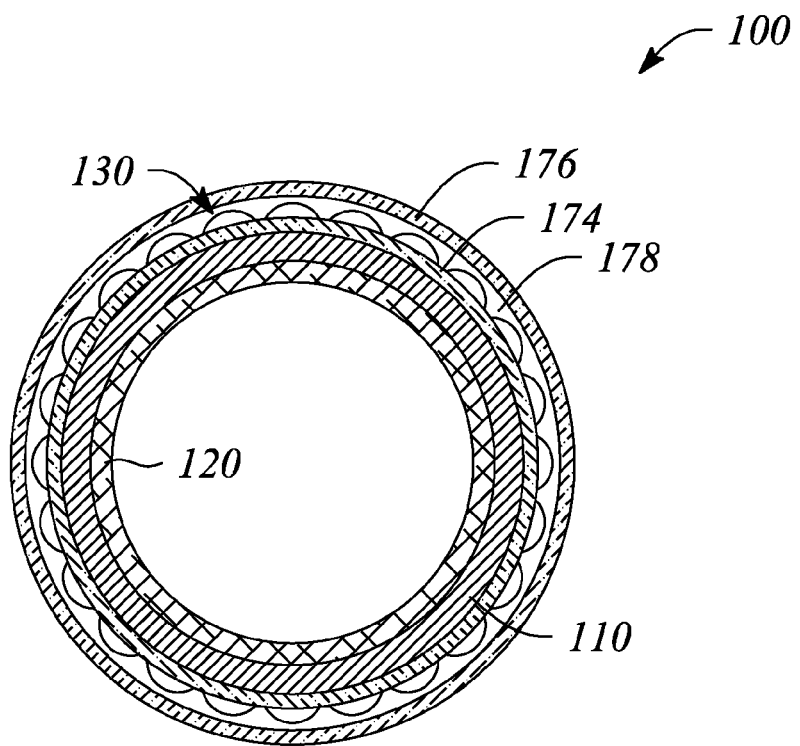
FIG. 7 illustrates a cross sectional view of a scattering spectroscopy nanosensor, according to yet another example consistent with the principles described herein.

FIG. 6 illustrates a cross sectional view of a scattering spectroscopy nanosensor 100, according to another example consistent with the principles described herein. FIG. 7 illustrates a cross sectional view of a scattering spectroscopy nanosensor 100, according to yet another example consistent with the principles described herein. In particular, the cross sectional views illustrated in both of FIGS. 6 and 7 depict a cross sections through the scattering spectroscopy nanosensor 100 that are substantially similar in orientation to the cross sectional view illustrated in FIG. 5A.

As illustrated in FIG. 6, the nanoscale-patterned sensor substrate 110 and protective covering 120 are disposed on a first portion 171 of an inside surface of a stent 170. An integral lens 130 (e.g., a lenslet of an array of lenslets) is disposed on second portion 172 of the inside surface of the stent 170 that is opposite the first portion 171. In another example (not illustrated), the integral lens 130 may be disposed on an outside surface of the second portion 172 instead of on an inside surface as illustrated in FIG. 6. The optical beam 140 and the optical stimulus 150 may be focused by the integral lens 130 onto a particular portion of the protective covering 120 and the nanoscale-patterned sensor substrate 110, as illustrated in FIG. 6.

As illustrated in FIG. 7, the nanoscale-patterned sensor substrate 110 and protective covering 120 are disposed on an inside surface of a stent 170. An integral lens 130 (e.g., a lenslet of an array of lenslets) is disposed on an outside surface of a first portion 174 of the stent 170. As illustrated, the integral lens 130 is covered by a second portion 176 of the stent 170. The second portion 176 may protect the lens 130 (e.g., prevent buildup of plaques, contaminants, etc., on a surface of the integral lens 130). Further, a space 178 between the first portion 174 and the second portion 176 of the stent 170 may be sealed and substantially filled with a fluid. For example, the fluid may be a gas (e.g., air or an inert gas) or a liquid (e.g., an oil). The fluid sealed between the first and second portions 174, 176 of the stent 170 may provide a predetermined (e.g., relatively large) refractive index change at a surface of the integral lens 130, for example. The predetermined refractive index change may one or both of enhance performance of and insure a particular optical characteristic of the integral lens 130 (e.g., focal length). For example, the fluid filled space 178 between the first and second portions 174, 176 of the stent 170 encapsulate the integral lens 130 to substantially insure optical characteristics of the integral lens 130 regardless of an environment surrounding the scattering spectroscopy nanosensor 100, according to some examples. Other configurations are clearly possible and are explicitly within the scope described herein.

In some examples, the optical beam 140 and optical stimulus 150 do not need to be aimed at or aligned with a particular lens 130 (e.g., in an array of lenses). Further the optical beam 140 and optical stimulus 150 may not need to be aimed or aligned in a manner that insures that they pass through or substantially near to a center axis of the lens 130. Instead, the alignment of the optical beam 140 and optical stimulus 150 may be substantially random, in particular, when a large number of lenses 130 are used and when there is a relatively large surface area of nanoscale-patterned sensor substrate 110 covered by the protective covering 120 available for interrogation, for example. In particular, the optical beam 140 followed by the optical stimulus 150 may be directed at the scattering spectroscopy nanosensor 100 in a first alignment (e.g., substantially random alignment) to remove the protective covering 120 and interrogate the nanoscale-patterned sensor substrate 100. If no optical scattering response signal 160 is received, then another attempt at interrogation may be made at another location on the scattering spectroscopy nanosensor 100 or using another alignment of the optical beam 140 and optical stimulus 150, for example.

In some examples, the scattering spectroscopy nanosensor 100 further comprises a fiducial marker (not illustrated). The fiducial marker may be used to facilitate alignment of one or both of the optical beam and the optical stimulus, according to various examples. In particular, the alignment is to facilitate in vivo for an implanted scattering spectroscopy nanosensor 100, according to some examples. In some examples, the fiducial marker may be a fluorescent fiducial marker that is imaged (e.g., using an imaging system) to determine an orientation and position of the scattering spectroscopy nanosensor 100. Once an orientation and position of the scattering spectroscopy nanosensor 100 is determined, an alignment of one or both of the optical beam and optical stimulus may be established using the determined orientation and position, for example. In some examples, the fiducial marker or markers (e.g., fluorescent fiducial markers) comprise a plurality dots and one or more cross-shaped fiducial markers. For example, the cross-shaped fiducial marker(s) may be located on one or both ends of the scattering spectroscopy nanosensor 100 (e.g., on one or both ends of the stent 170 upon which the nanoscale-patterned sensing substrate 110 is disposed). The dots may be arranged around a circumference of the stent 170 in an angular orientation, for example. Together, the cross-shaped fiducial marker(s) and the angularly oriented dots may allow for a substantially unambiguous determination the orientation and the location of the scattering spectroscopy nanosensor 100 to be made when the fiducial markers are imaged, according to some examples.

Figure 8:
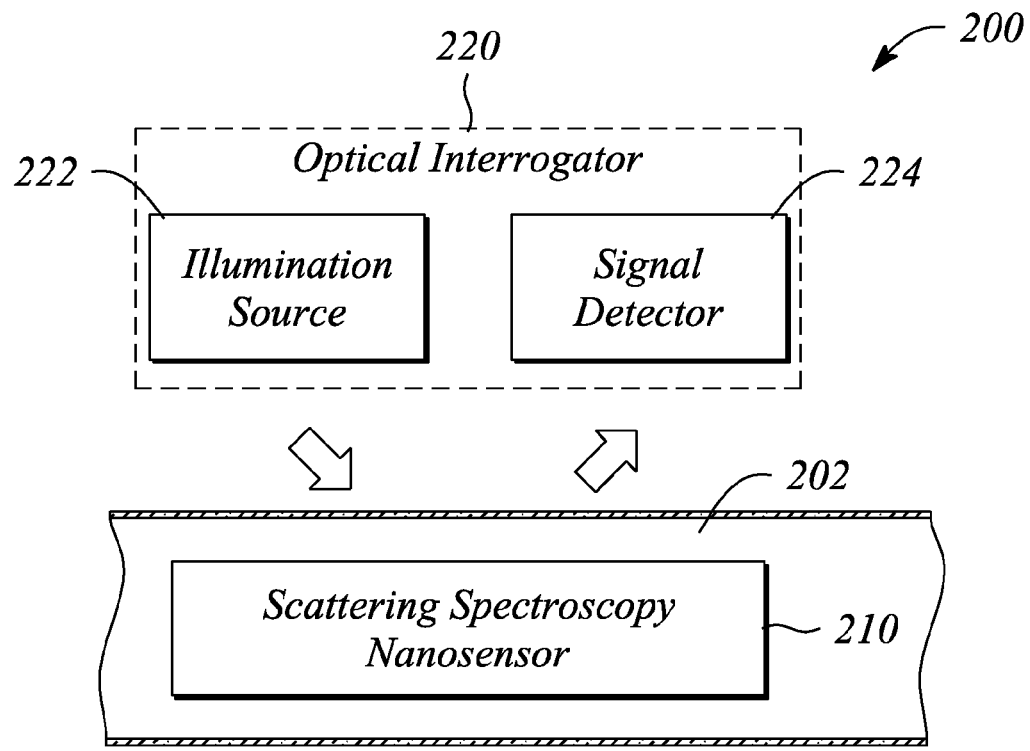
FIG. 8 illustrates a block diagram of a nanosensor system, according to an example consistent with the principles described herein.

FIG. 8 illustrates a block diagram of a nanosensor system 200, according to an example consistent with the principles described herein. As illustrated, the nanosensor system 200 comprises a scattering spectroscopy nanosensor 210. According to various examples, the scattering spectroscopy nanosensor 210 comprises a nanoscale-patterned sensing substrate and one or both of a protective covering for the nanoscale-patterned sensing substrate and an integral lens. The nanoscale-patterned sensing substrate is configured to produce an optical scattering response signal indicative of the presence of an analyte when interrogated by an optical stimulus. The integral lens is integral to the scattering spectroscopy nanosensor 210. In some examples, the scattering spectroscopy nanosensor 210 is configured to be implantable inside a fluid conduit 202.

In some examples, the scattering spectroscopy nanosensor 210 is substantially similar to the scattering spectroscopy nanosensor 100 described above. In particular, the nanoscale-patterned sensing substrate may be substantially similar to the nanoscale-patterned sensing substrate 110 described above with respect to the scattering spectroscopy nanosensor 100. For example, the nanoscale-patterned sensing substrate may comprise a surface enhanced Raman spectroscopy (SERS) substrate. The optical scattering response signal may be a Raman scattering signal produced by an interaction between the analyte and the SERS substrate, according to some examples.

Further, the protective covering may be substantially similar to the protective covering 120 described above with respect to the scattering spectroscopy nanosensor 100, according to some examples. In particular, the protective covering is configured to cover and protect the nanoscale-patterned sensor substrate and is further selectively removable by exposure to an optical beam incident on the protective covering, according to various examples. In some examples, exposure to the optical beam selectably removes only a portion of the protective covering in a vicinity of the optical beam while in other examples, the entire protective covering is selectably removed by the optical beam exposure. According to various examples, selective removal using the optical beam may be provided by one or more of ablation of the exposed portion of the protective covering, photo-induced alteration of an exposed portion of the protective covering, thermal-induced alteration of an exposed portion of the protective covering, and any of a variety of other mechanisms, including but not limited to those described above with respect to the protective covering 120.

When the protective covering is in place, the nanoscale-patterned sensor substrate is protected and 'inactivated' with the protective covering substantially preventing an analyte from interacting with (e.g., being adsorbed onto) the nanoscale-patterned sensor surface. When the protective covering is removed, interrogation with the optical stimulus 'activates' the nanoscale-patterned sensor substrate such that the optical response signal (e.g., a SERS scattering response signal) may be generated as a result of an interaction between the analyte and the nanoscale-patterned sensor substrate.

Further still, the integral lens of the scattering spectroscopy nanosensor 210 may be substantially similar to the integral lens 130 described above with respect to the scattering spectroscopy nanosensor 100, according to some examples. In particular, one or more of the optical stimulus, the optical beam and the optical scattering response signal may be configured to pass through the integral lens, according to various examples. In some examples, the integral lens may focus the optical beam onto the protective covering to facilitate selective removal thereof. In some examples, the integral lens may focus the optical stimulus onto a portion of the nanoscale-patterned sensor substrate. For example, the portion may a portion exposed by selective removal of the protective cover by the optical beam. Further, the optical scattering response signal may be collected, and in some examples substantially collimated by the integral lens, in some examples.

In some examples, the scattering spectroscopy nanosensor 210 may further comprise a stent. The stent may be substantially similar to the stent 170 described above with respect to scattering spectroscopy nanosensor 100, for example. In particular, in some examples, the integral lens may be integral to the stent, and the nanoscale-patterned sensor substrate and the protective covering may be disposed on a surface of the stent, as described above, for example. The stent may facilitate implanting the scattering spectroscopy nanosensor 210 (e.g., in the fluid conduit 202) to facilitate in vivo sensing of an analyte, for example.

In some examples, the scattering spectroscopy nanosensor 210 of the nanosensor system 200 is configured to detect a plurality of different analytes. In some examples, the scattering spectroscopy nanosensor 210 is configured to distinguish between the different analytes. For example, the nanoscale-patterned sensor substrate of the scattering spectroscopy nanosensor 210 may have a plurality of separate regions.

Different ones of the regions of the plurality may be functionalized to be selective for a different analyte of a plurality of analytes and to produce an optical scattering response signal indicative of the respective different analyte. Spatial separation between the regions may facilitate distinguishing an optical scattering response signal produced by a first analyte specific to a first functionalization in a first region from an optical scattering response signal produced by a second analyte specific to a second functionalization in a second region of the nanoscale-patterned sensor substrate, for example.

As illustrated in FIG. 8, the nanosensor system 200 further comprises an optical interrogator 220. According to some examples, the optical interrogator 220 comprises an illumination source 222. The illumination source 222 is configured to illuminate the scattering spectroscopy nanosensor 210. In particular, the illumination source 222 is configured to provide one or both of the optical stimulus to illuminate the nanoscale-patterned sensing substrate and the optical beam to illuminate the protective covering. In some examples, the nanoscale-patterned sensing substrate may be illuminated by the illumination source 222 in view while the scattering spectroscopy nanosensor 210 is implanted in the fluid conduit.

In some examples, the illumination source 222 is configured to produce an infrared optical signal to illuminate the scattering spectroscopy nanosensor 210. The infrared optical signal may be one or both of the optical beam to illuminate the protective covering and the optical stimulus to illuminate the nanoscale-patterned sensing substrate, according to various examples. For example, infrared radiation may penetrate biological tissue (e.g., human tissue) to a depth of about 10-15 millimeters (mm) facilitating in vivo illumination and interrogation of the scattering spectroscopy nanosensor 210. In other examples, the illumination source 222 is configured to produce an optical signal comprising other optical frequencies instead of or including infrared.

In some examples, the optical interrogator 220 further comprises signal detector 224. The signal detector 224 is configured detect the optical scattering response signal emitted by the scattering spectroscopy nanosensor 210 that is indicative of the analyte. For example, the signal detector 224 may be a Raman scattered signal detector (e.g., a spectrometer) configured to detect the Raman scattered signal emitted by a SERS nanoscale-patterned sensing substrate. In some examples, one or both of the illumination source 222 and the signal detector 224 are external to the fluid conduit in which the scattering spectroscopy nanosensor 210 is to be implanted. For example, if the fluid conduit is inside an organism, one or both of the illumination source 222 and signal detector 224 may be located external to the organism.

Figure 9:
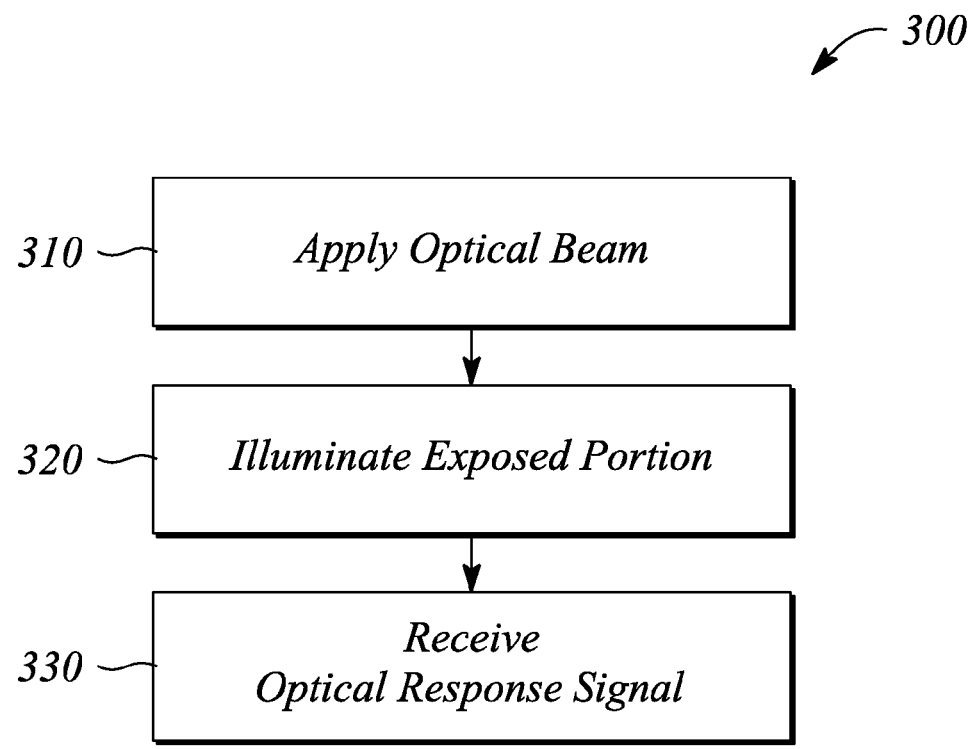
FIG. 9 illustrates a flow chart of a method of sensing an analyte using scattering spectroscopy, according to an example consistent with the principles described herein.

FIG. 9 illustrates a flow chart of a method 300 of sensing an analyte using scattering spectroscopy, according to an example consistent with the principles described herein. As illustrated, the method 300 of sensing an analyte comprises applying 310 an optical beam to a scattering spectroscopy nanosensor. In some examples, the scattering spectroscopy nanosensor is substantially similar to the scattering spectroscopy nanosensor 100, described above. In particular the scattering spectroscopy nanosensor may comprise a nanoscale-patterned sensing substrate covered by a protective covering. When applied, the optical beam is configured to selectively remove a region of the protective covering. Selective removal of the protective covering exposes a portion of the nanoscale-patterned sensor substrate. Specifically the exposed portion corresponds to a portion of the nanoscale-patterned sensor substrate underlying the removed region of the protective covering. Applying 310 the optical beam to remove the region of the protective covering substantially activates the exposed portion of the nanoscale-patterned sensor substrate that was previously rendered inactive by the protective covering prior to applying 310 the optical beam, according to various examples.

The method 300 of sensing an analyte further comprises illuminating 320 the exposed portion of the nanoscale-patterned sensor substrate with an optical stimulus. In particular, when the protective covering is removed, a fluid that may include an analyte to be investigated flows in contact with the exposed surface of the nanoscale-patterned sensor substrate. Illuminating 320 the exposed portion is configured to produce an optical scattering response signal indicative of the presence of the analyte, according to various examples. According to some examples, illuminating 320 the exposed portion may be provided by an illumination source that is substantially similar to the illumination source 222 described above with respect to the nanosensor system 200, described above. In some examples, the illumination source may also provide the optical beam employed in applying 310.

In some examples, the nanoscale-patterned sensing substrate comprises a surface enhanced Raman spectroscopy (SERS) substrate and the optical scattering response signal is a Raman scattered signal produced by an interaction between the analyte and the SERS substrate. For example, the SERS substrate may be substantially similar to the SERS substrate described above comprising nanorods 112 arranged in an array.

As illustrated in FIG. 9, in some examples, the method 300 of sensing an analyte using scattering spectroscopy further comprising receiving 330 the optical response signal emitted by the illuminated 320 nanoscale-patterned sensing substrate. In some examples, receiving 330 the optical response signal may be performed by a signal detector. For example, the signal detector may be substantially similar to the signal detector 224 described above with respect to the nanosensor system 200. In some examples, one or both of the illumination source and the signal detector are located external to the fluid conduit containing the scattering spectroscopy nanosensor. In some examples, the scattering spectroscopy nanosensor further comprises an integral lens, wherein one or more of the optical beam, the optical stimulus and the optical scattering response signal pass through (e.g., being focused by) the integral lens. In some examples, the integral lens may be substantially similar to the integral lens 130 described above with respect to the scattering spectroscopy nanosensor 100, described above.

Thus, there have been described examples of a scattering spectroscopy nanosensor, a nanosensor system and a method of in vive sensing using a scattering spectroscopy. It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A scattering spectroscopy nanosensor comprising:
  a nanoscale-patterned sensing substrate to produce an optical scattering response signal indicative of a presence of an analyte when interrogated by an optical stimulus; and
  a protective covering to cover and protect the nanoscale-patterned sensing substrate, the protective covering is to be selectably removed by exposure to an optical beam incident on the protective covering,
  wherein the protective covering is to prevent the analyte from interacting with the nanoscale-patterned sensing substrate prior to being removed.

2. The scattering spectroscopy nanosensor of claim 1, wherein nanoscale-patterned sensing substrate comprises a surface enhanced Raman spectroscopy (SERS) substrate, and wherein the optical scattering response signal is a Raman scattered signal to be produced by the analyte.

3. The scattering spectroscopy nanosensor of claim 2, wherein the SERS sensing substrate comprises a plurality of nanorods arranged in an array, at least some of the nanorods having a metallic tip to adsorb the analyte, the tip being at a free end of the nanorod opposite to an end that is attached to a support.

4. The scattering spectroscopy nanosensor of claim 1, wherein the protective covering is to be selectively removed by one of (1) ablation of a material of the protective covering by the optical beam and (2) an alteration of a portion of the protective covering by the optical beam, the alteration being one or both of a photo-induced and thermal-induced.

5. The scattering spectroscopy nanosensor of claim 1, further comprising a fiducial marker to facilitate alignment of one or both of the optical beam and the optical stimulus.

6. The scattering spectroscopy nanosensor of claim 1, further comprising a lens that is integral with the scattering spectroscopy nanosensor, the integral lens to one or more of focus the optical beam onto the protective covering, focus the optical stimulus on a portion of the nanoscale-patterned sensing substrate exposed by selective removal of the protective cover, and collect the optical scattering response signal.

7. The scattering spectroscopy nanosensor of claim 1, further comprising a stent to be implanted in a fluid conduit, the nanoscale-patterned sensing substrate being disposed on a surface of the stent.

8. A nanosensor system comprising the scattering spectroscopy nanosensor of claim 1, the nanosensor system further comprising:
   an illumination source to illuminate the nanoscale-patterned sensing substrate, illumination from the illumination source to one or both of selectably remove the protective covering and produce the optical stimulus; and
   a signal detector to detect the optical scattering response signal emitted by the scattering spectroscopy nanosensor indicative of the analyte.

9. The nanosensor system of claim 8, wherein the nanoscale-patterned sensing substrate is to be implanted in a fluid conduit to provide in vivo sensing of the analyte, and wherein one or both of the illumination source and the signal detector are external to the fluid conduit.

10. The system of claim 8, wherein the illumination source is to illuminate the nanoscale-patterned sensing structure to selectively remove the protective covering to illuminate the nanoscale-patterned sensing substrate.

11. The system of claim 8, wherein the illumination source is operable in a first mode to selectively remove the protective covering to illuminate the nanoscale-patterned sensing substrate and a second mode to illuminate the nanoscale-patterned sensing substrate to produce the optical stimulus.

12. A nanosensor system comprising:
   a scattering spectroscopy nanosensor comprising a nanoscale-patterned sensing substrate and one or both of a protective covering to cover the nanoscale-patterned sensing substrate and an integral lens, the nanoscale sensing substrate to produce an optical scattering response signal indicative of an analyte when interrogated by an optical stimulus, the protective covering being selectively removable by exposure to an optical beam; and
   an optical interrogator comprising an illumination source and a signal detector, the illumination source to provide one or both of the optical stimulus and the optical beam, the signal detector to detect the optical scattering response signal,
   wherein one or more of the optical stimulus, the optical beam and the optical scattering response signal are to pass through the integral lens if present.

13. The nanosensor system of claim 12, wherein the scattering spectroscopy nanosensor is to be implanted inside a fluid conduit, one or both of the illumination source and the signal detector being external to the fluid conduit.

14. The nanosensor system of claim 12, wherein the nanoscale patterned sensing substrate comprises a surface enhanced Raman spectroscopy (SERS) substrate, and wherein the optical scattering response signal is a Raman scattered signal produced by an interaction between the analyte and the SERS substrate.

15. The nanosensor system of claim 12, wherein the scattering spectroscopy nanosensor comprises the protective covering, the protective covering is to be selectively removed either by ablation or by alteration of a material of the protective covering upon exposure to the optical beam, the alteration comprising one or both of a photo-induced and thermal-induced alteration of the material.

16. A method of sensing an analyte using scattering spectroscopy, the method comprising:
   applying an optical beam to a scattering spectroscopy nanosensor, the scattering spectroscopy nanosensor comprising a nanoscale-patterned sensor substrate covered by a protective covering, the optical beam to selectively remove a region of the protective covering, wherein selective removal exposes a portion of the nanoscale-patterned sensor substrate underlying the removed region of the protective covering; and
   illuminating the exposed portion of the nanoscale-patterned sensor substrate with an optical stimulus to produce an optical scattering response signal indicative of the presence of an analyte.

17. The method of sensing an analyte using scattering spectroscopy of claim 16, further comprising:
   receiving the optical scattering response signal emitted by the illuminated nanoscale-patterned sensing substrate using a signal detector, one or both of the illumination source and the signal detector being located external to a fluid conduit containing the scattering spectroscopy nanosensor,
   wherein the scattering spectroscopy nanosensor further comprises an integral lens, one or more of the optical beam, the optical stimulus and the optical scattering response signal passing through the integral lens.

* * * * *